United States Patent [19]

Peers-Trevarton

[11] Patent Number: 4,583,543

[45] Date of Patent: Apr. 22, 1986

[54] UPSIZING ADAPTER

[75] Inventor: Charles A. Peers-Trevarton, Coral Springs, Fla.

[73] Assignee: Cordis Corporation, Miami, Fla.

[21] Appl. No.: 491,608

[22] Filed: May 4, 1983

[51] Int. Cl.$^4$ .............................................. A61N 1/00
[52] U.S. Cl. ................................................ 128/419 P
[58] Field of Search ....... 128/419 P, 419 PG, 419 PS, 128/419 R, 784–786; 339/278 T

[56] References Cited

U.S. PATENT DOCUMENTS

| | | | |
|---|---|---|---|
| 4,027,678 | 6/1977 | van Oostveen et al. ............. | 128/419 |
| 4,105,037 | 8/1978 | Richter et al. .................... | 128/419 P |
| 4,202,592 | 5/1980 | Rullier et al. ................. | 128/419 P X |
| 4,226,244 | 10/1980 | Coury et al. ......................... | 128/419 |
| 4,236,525 | 12/1980 | Sluetz et al. ........................ | 128/419 |
| 4,259,962 | 4/1981 | Peers-Trevarton .................. | 128/419 |
| 4,301,805 | 11/1981 | Peers-Trevarton et al. ... | 128/419 P |
| 4,423,732 | 1/1984 | Tarjan et al. ..................... | 128/419 P |
| 4,445,511 | 5/1984 | Cowdery et al. ................ | 128/419 P |

FOREIGN PATENT DOCUMENTS 3118090 11/1982 Fed. Rep. of Germany ... 128/419 P
2104314 3/1983 United Kingdom ............ 128/419 P

*Primary Examiner*—Kyle L. Howell
*Assistant Examiner*—Angela D. Sykes
*Attorney, Agent, or Firm*—Henry W. Collins; Thomas R. Vigil

[57] ABSTRACT

The upsizing adapter is used for electrically and mechanically coupling (a) a small size terminal electrode assembly having at least one ring electrode and a pin electrode and being situated at the proximal end of a pacing lead to (b) a large size terminal electrode assembly socket in a pacer having at least first and second electrical contacts therein for making contact with a large size terminal electrode assembly having a ring electrode and a pin electrode. The adapter comprises a tubular body and a first electrical coupling for electrically coupling a ring electrode of a small size terminal electrode assembly with a first electrical contact in a pacer and a second electrical coupling for electrically coupling a terminal pin electrode of a small size terminal electrode assembly with a second electrical contact in the pacer terminal electrode assembly socket.

22 Claims, 3 Drawing Figures

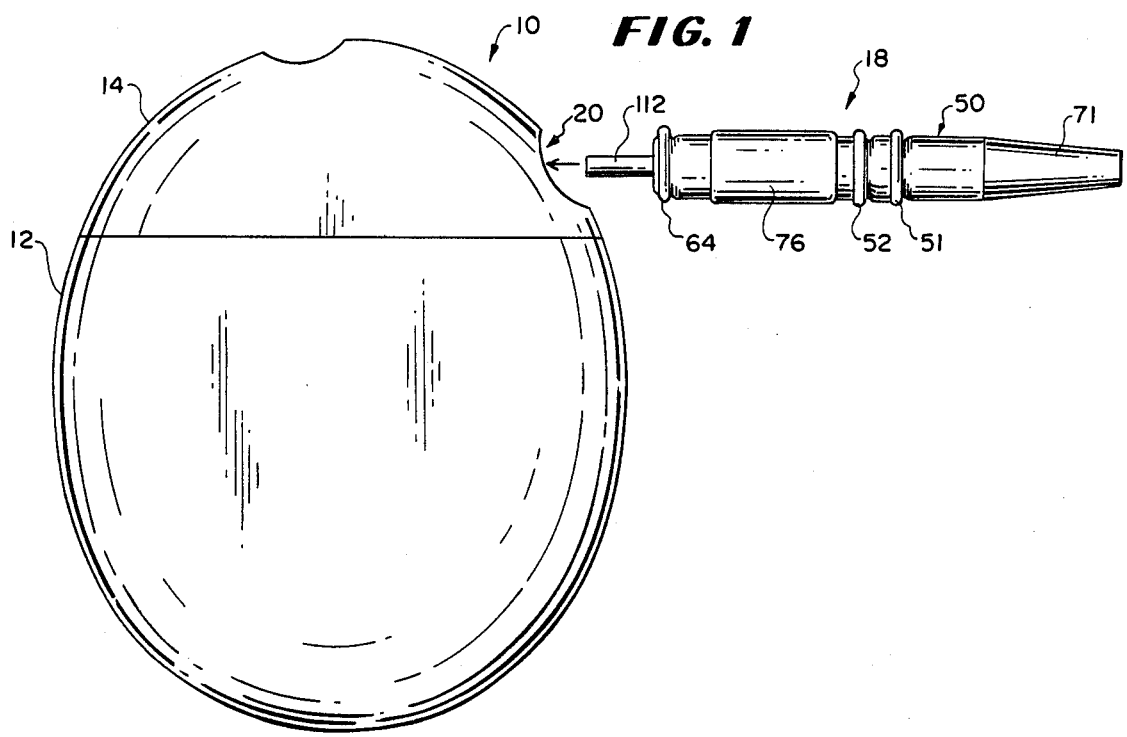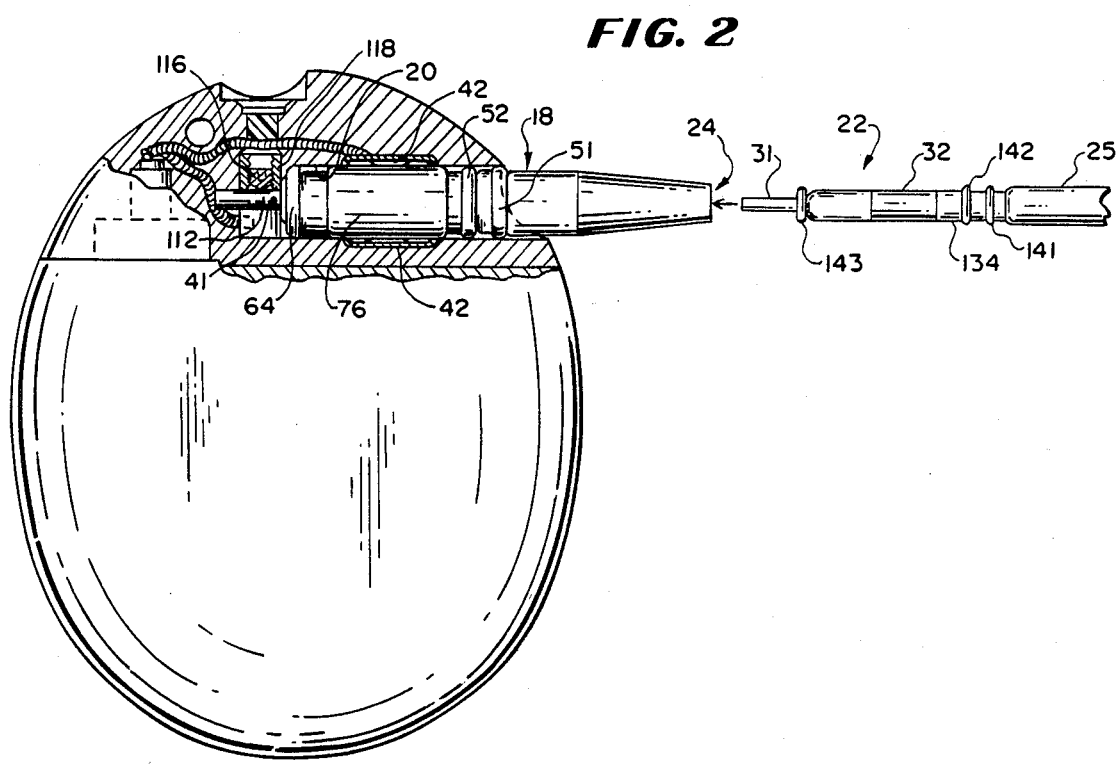

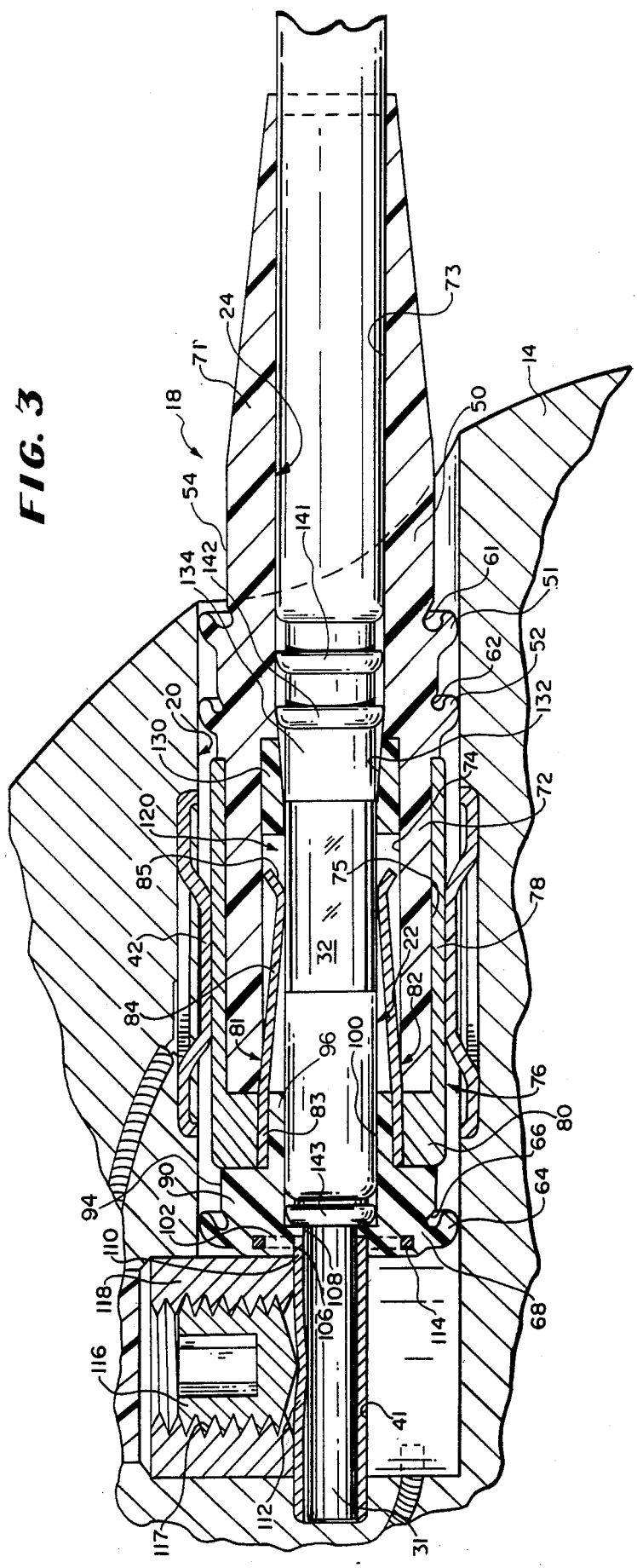

UPSIZING ADAPTER

BACKGROUND OF THE INVENTION

1. Field of the Invention

The present invention relates to an upsizing adapter for electrically and mechanically coupling (a) a small size terminal electrode assembly having at least one ring electrode and a pin electrode and being situated at the proximal end of a pacing lead to (b) a large size terminal electrode assembly socket in a pacer having first and second electrical contacting means therein for contact with a ring electrode and pin electrode on a large size terminal electrode assembly.

2. Description of the Prior Art

Heretofore, various structures have been proposed for connecting a terminal pin assembly at the proximal end of a pacing lead assembly to a terminal pin assembly socket in a pacer.

For example, in U.S. Pat. No. 4,207,678, there is disclosed a connector for connecting a pin electrode to a pacer where the pacer with a socket therein and the pin electrode are derived from different manufacturers and are normally not adapted for connection one to another. The connector has a coil therein dimensioned to receive the pin electrode and has a smaller diameter pin extending therefrom for being received in the pacer socket. The connector is adapted to permit connection or disconnection as the connector is rotated.

In U.S. Pat. No. 4,259,962, there is disclosed, a tubular connector connected to the proximal end of a pacing lead assembly and having axially spaced inner and outer resilient rings for sealing engagement with the socket wall of a pacer neck.

In U.S. Pat. No. 4,226,244, there is disclosed, a preformed connector with an encapsulated terminal for attachment to a pacer. The preformed connector eliminates the use of epoxy or other similar substances to encapsulate the terminal after attachment of the terminal to the pacer.

Also, in U.S. Pat. No. 4,236,525, there is disclosed a proximal connector of a pacing lead assembly which connector is mounted in a socket in a pacer neck and is movable to change connections between contacts on the connector and contacts in the socket thereby to change the function of distal electrodes coupled by a pacing lead to the connector contacts.

As will be described in greater detail hereinafter, the upsizing adapter of the present invention differs from the structures disclosed in the patents referred to above by providing a structure for establishing both mechanical and electrical connections between a small size terminal electrode assembly located at the proximal end of a pacing lead assembly and having two electrodes and a large size terminal electrode assembly socket in a pacer having first and second electrical contacting means in the socket.

SUMMARY OF THE INVENTION

According to the invention, there is provided an upsizing adapter for electrically and mechanically coupling (a) a small size terminal electrode assembly having at least one ring electrode and a pin electrode and being situated at the proximal end of a pacing lead to (b) a large size terminal electrode assembly socket in a pacer having at least first and second electrical contacting means therein for making contact with a large size terminal electrode assembly having, a ring electrode and a pin electrode, said adapter comprising: first electrical coupling means for electrically coupling a ring electrode of a small size terminal electrode assembly with first electrical contact means in a large size terminal electrode assembly socket in a pacer and second electrical coupling means for electrically coupling a terminal pin electrode of a small size terminal electrode assembly with second electrical contact means in the terminal electrode assembly socket.

Preferably, the adapter comprises a generally tubular body made of an insulating material and is sized to fit into the large size terminal assembly electrode socket, the interior of said body defining part of a small size terminal electrode assembly socket of said adapter adapted to receive the small size terminal electrode assembly therein.

BRIEF DESCRIPTION OF THE DRAWINGS

FIG. 1 is a side elevational view of a conventional pacer and shows an adapter constructed according to the teachings of the present invention positioned to be inserted into the pacer.

FIG. 2 is a partial sectional view of the pacer shown in FIG. 1 and shows the adapter shown in FIG. 1 received in an electrode assembly socket of the pacer.

FIG. 3 is a fragmentary sectional view of the pacer shown in FIG. 1 with the adapter received in the pacer socket and the small size terminal electrode assembly received in a socket of the adapter.

DESCRIPTION OF THE PREFERRED EMBODIMENT

Referring now to the drawings in greater detail, there is illustrated in FIG. 1 a pacer 10. The pacer 10 is of conventional construction and includes a power source and electrical circuitry necessary for generating electrical signals which are supplied to a pacing lead (not shown). The power source and electrical circuitry are contained within a main body 12 of the pacer 10. An upper body portion 14 of the pacer 10 is adapted to receive a large size terminal electrode assembly (not shown) which is mounted at the proximal end of a pacing lead and which has the general shape of adapter 18 shown adjacent the pacer 10. The adapter 18 is constructed in accordance with the teachings of the present invention as will be described in greater detail below.

The upper body portion 14 is constructed with a terminal electrode assembly socket 20 (FIG. 2) which is constructed and designed primarily to receive a large size terminal electrode assembly therein. However, terminal electrode assemblies of more recent construction are of a smaller cross-sectional extent than pacer terminal electrode assembly sockets 20 in earlier pacer constructions. As will now be described, the present invention teaches the construction and use of the adapter 18 to provide an electrical and mechanical connection between a small size terminal electrode assembly 22 (FIG. 2) and a larger sized pacer terminal electrode assembly socket 20.

The adapter 18 is adapted to be inserted into the terminal electrode assembly socket 20 in the pacer 10 as shown in FIG. 2. and the smaller terminal electrode assembly 22 is inserted into an adapter socket 24 (FIG. 3) in the adapter 18 as shown in FIG. 3. In this way, the smaller terminal electrode assembly 22 mounted at the proximal end of a pacing lead 25 is received and held in a larger size socket 20 in an existing pacer 10 with the adapter 18 providing electric connection from terminals 31, 32 (FIG. 2) of the terminal electrode assembly 22 and contacts 41 and 42 (FIG. 2) in the pacer terminal electrode assembly socket 20.

Referring to FIG. 3, adapter 18 is generally tubular in shape and includes a generally tubular body 50 which is made of a stiff but resilient insulating material and which has two annular sealing rings 51 and 52 on the exterior surface 54 thereof. Immediately forward and adjacent to each annular sealing ring 51, 52 is an annular groove 61, 62. Before insertion of the adapter 18 into the socket 20, the annular rings 51, 52 have a diameter greater than the interior diameter of the pacer terminal electrode assembly socket 20. When the adapter 18 is inserted into the pacer terminal electrode assembly socket 20, each annular ring 51, 52 deflects resiliently over and toward the adjacent annular grooves 61, 62 so that the adapter 18 is sealingly engaged in the terminal electrode assembly socket 20. An additional annular ring 64 and groove 66 are provided on a barrel member 68 at the rear end of the adapter 18.

It will be understood that any number of annular rings may be provided and such rings and grooves are of the type disclosed in U.S. Pat. No. 4,259,962.

The body 50 of the adapter 18 has a forward sleeve portion 71 and a rearward sleeve portion 72. The sleeve portion 71 has an interior cylindrical cavity 73 sized to fit over the sheath of the pacing lead 25. The rearward sleeve portion 72 has a larger interior cylindrical cavity 74 and the cavities 73 and 74 define part of the adapter socket 24.

Outer surface 75 of the rearward sleeve portion 72 has a smaller outer diameter than the outer diameter of the surface 54 as shown to receive thereon metal ring electrode 76 adapted to make contact with ring shaped electrical contact 42 in the pacer socket 20.

The outside diameter of the ring electrode 76 is slightly greater than the outside diameter of the tubular body surface 54 of the adapter 18 in order to provide good electrical connection with the contact 42 in the pacer terminal electrode assembly socket 20. The ring electrode 76 has a thin sleeve portion 78 and a thicker portion 80 which is positioned adjacent the rear end of the tubular body 50 and at least two, electrically conductive fingers 81,82 which extend into the cylindrical cavity 74. Each finger 81,82 has a fixed end 83 which is attached to the thicker portion 80 and a free end 84 which first extends axially and radially inwardly into the cavity 74 for making electrical contact with the small size terminal electrode assembly 22.

Each finger 81,82 then has a bent end 85 which extends in a direction axially and radially outwardly from the axis of the adapter 18 to the side wall of cavity 74.

In operation, when the adapter 18 is inserted into the pacer socket 20 and the small terminal electrode assembly 22 is inserted into the adapter socket 24, the fingers 81,82 make electrical contact with ring contact 32 for conduction of electricity between ring contact 32 through fingers 81,82, portion 80, portion 78 and ring electrode 76 to electrical contact 42 in pacer socket 20.

The adapter 18 further includes a barrel member 68 which is positioned at the rear end of the adapter 18 and includes a main body 90 having an outer cylindrical surface 94 with a diameter generally the same as the outer diameter of the cylindrical surface 54 of the forward sleeve portion 71 of tubular body 50. Extending forwardly from the main body 90 is a reduced in diameter portion 96 which is received within the thicker portion 80 of the metal electrode ring 76. In this respect, the reduced in diameter portion 96 serves to urge the rear end 83 of the fingers 81, 82 against the inner surface of the thicker ring portion 80 if they are not fixed to the thicker ring portion 80 by soldering or spot welding.

Within the barrel member 68 is formed a cylindrical cavity 100 which extends from the forward end of the member 68 through the reduced in diameter portion 96 toward the rear end of the adapter 18 and to an end wall portion 102 of the barrel member 68. Extending through the wall portion 102 is a countersunk opening having a smaller in diameter portion 106 of the countersunk opening sized to receive therethrough the terminal pin contact 31 of the small sized terminal electrode assembly 22 and a countersunk, larger diameter portion 108 of the opening has received therein one end 110 of a metal tube 112. To reinforce the mounting of the tube 112 in the wall portion 102 of the barrel member 68 the wall portion 102 can have molded therein a metal ring 114 extending around the sleeve end 110. Alternatively, the forward end 110 of the tube 112 can have a spider type flange formed thereon with the ring 114 being part of the flange which is connected by spokes (not shown) to the end 110 of the tube 112.

The tube 112 is received within a metal socket 41 in the pacer 10, the socket 41 defining the electrical contact 41.

An Allen set screw 116 is received within a threaded bore 117 in a body 118 containing the metal socket/contact 41. When threaded into the body 118, a pointed tip of the screw 116 forces a side wall portion of metal tube 112 downwardly into contact with terminal pin 31 of the small size terminal electrode assembly 22 and through pin 31 forces another, lower, side wall portion of tube 112 against a surface portion of metal socket/contact 41. In this way, a secure electrical and mechanical connection is made between terminal pin 31 and metal socket/contact 41.

The cylindrical cavity 102 in the barrel member 68 has a diameter approximately equal to the diameter of the cylindrical cavity 73 within the forward sleeve portion 71 of the tubular body 50. In this way, the interior of the metal tube 112, the cylindrical cavity 102 of the barrel member 68 and the cavities 74 and 73 within the tubular body 50 form socket 24 of the adapter 18.

It will be noted that the annular space 120 between the outer surface of small size terminal electrode assembly 22 and the cavity 74 provide a space 120 within which the portion 84 and 85 of the fingers 81 and 82 can be deflected when the small size terminal electrode assembly 22 is inserted into the socket 24 of the adapter 18. When this is done, it will be noted that the ring shaped electrical contact 32 is positioned to engage and make contact with the fingers 81 and 82 adjacent the bent ends 84 thereof.

A collar 130 is positioned in the forward end of the cylindrical cavity 74 and has a tapered or semi-conical surface 132 so that it will make an interference fit with a portion 134 of the small sized terminal electrode assembly 22 having the ring shaped electrical contact 32 thereon.

Further, it will be noted that the small size terminal electrode assembly 22 is of the type with annular sealing rings 141, 142 and 143 similar in construction and function to the sealing rings 51, 52 and 64. In this way, a fluid tight seal is established between the small size terminal pin electrode assembly 22 and the socket 24 within the adapter 18 while at the same time the annular sealing rings 51, 52 and 64 on the exterior surfaces 54 and 94 of the adapter 18 establish a fluid tight seal with the interior of the pacer socket 20.

From the foregoing description, it will be apparent that the upsizing adapter 18 of the present invention has a number of advantages, some of which have been described above and others of which are inherent in the invention.

Also, it will be apparent that modifications can be made to the upsizing adapter 18 of the present invention without departing from the teachings of the present invention. Accordingly, the scope of the invention is only to be limited as necessitated by the accompanying claims.

I claim:

1. An upsizing adapter for electrically and mechanically coupling (a) a small size terminal electrode assembly having at least one ring electrode and a pin electrode and being of the type which is mounted on the end of a pacing lead to (b) a large size terminal electrode assembly socket in a pacer having at least first and second electrical contact means therein for making contact with a large size terminal electrode assembly having a ring electrode and a pin electrode, said adapter comprising: first electrical coupling means for electrically coupling a ring electrode of a small size terminal electrode assembly with said first electrical contact means in a large size terminal electrode assembly socket in a pacer and, second electrical coupling means for electrically coupling a terminal pin electrode of a small size terminal electrode assembly with said second electrical contact means in the terminal electrode assembly socket.

2. The adapter of claim 1 comprising a generally tubular body made of an insulating material having a proximal end and a distal end and being sized to fit into the large size terminal electrode assembly socket, said body having a hollow interior part of which defines a small size terminal electrode assembly receiving socket of said adapter which is adapted to receive the small size terminal electrode assembly.

3. The adapter of claim 2 wherein said tubular body has a forward sleeve portion adapted to be received over the end of a pacing lead and rearward sleeve portion, said first electrical coupling means being positioned on the interior and exterior of said rearward sleeve portion.

4. The adapter of claim 3 wherein said rearward sleeve portion includes a sleeve end portion and said first electrical coupling means includes a metal sleeve extending about said rearward sleeve portion, said metal sleeve having a thicker portion thereof abutting said sleeve end portion, and contact means which extend from said thicker portion into said rearward sleeve portion for contacting the ring electrode of the small size terminal electrode assembly received in said small size terminal electrode socket, the outer surface of said metal sleeve being sized to engage and make contact with the first electrical contact means in the large size terminal electrode socket in the pacer.

5. The adapter of claim 4 wherein said contact means comprise one or more deflectable metal fingers.

6. The adapter of claim 5 wherein each deflectable metal finger extends axially and radially inwardly of the axis of said rearward sleeve portion into said rearward sleeve portion and has a bent end extending axially and radially outwardly of the axis of said rearward sleeve portion.

7. The adapter of claim 4 including a barrel member made of insulated material received within said thicker portion of said metal sleeve and having an inner cylindrical cavity sized to fit closely about the small size terminal electrode positioned assembly and a rear wall with an opening therein sized to receive therethrough a pin electrode at the end of the small size terminal electrode assembly.

8. The adapter of claim 7 wherein said barrel member has a reduced in diameter portion which is received in said thicker portion of said metal sleeve and a larger diameter portion extending rearwardly to said rear wall.

9. The adapter of claim 8 wherein said second electrical coupling means comprise a metal tube having one end fixed in said opening in said rear wall of said barrel member, extending rearwardly from said barrel member and being sized to receive and make contact with a pin at the end of the small size terminal electrode assembly, the outer surface of said metal tube being sized to engage and make contact with said second electrical contact means in the large size terminal electrode assembly socket in the pacer.

10. The adapter of claim 9 including reinforcing means in said rear wall around said opening for reinforcing the mounting of said one end of said metal tube in said opening.

11. The adapter of claim 8 wherein said barrel member has an annular deflectable sealing ring extending around said larger diameter portion and an annular groove adjacent to and forward of said ring, formed in said larger diameter portion.

12. The adapter of claim 4 wherein a first cylindrical chamber within said forward sleeve portion of said tubular body is sized to receive and fit over the small size terminal electrode assembly and a second cylindrical chamber within said rearward sleeve portion of said tubular body having a greater interior diameter than said first cylindrical chamber to receive said contact means therein.

13. The adapter of claim 12 including a collar in said second cylindrical chamber adjacent said first cylindrical chamber, said collar having a conical or tapered inner surface sized and configured to make an interference fit with a small size terminal electrode assembly adapted to be received therein.

14. The adapter of claim 3 wherein said forward sleeve portion has at least one annular deflectable sealing ring extending around said tubular body and at least one annular groove adjacent to and forward of said ring forming said forward sleeve portion.

15. The adapter of claim 2 wherein said first electrical coupling means comprises an electrically conductive ring extending around said tubular body, said ring adapted to be electrically and mechanically connected to at least one contact element within said small sized terminal electrode socket for contacting the ring electrode on the small size terminal electrode assembly.

16. The adapter of claim 15 wherein a plurality of electrical contact elements are provided, each being in the shape of a deflectable finger having one end fixed to and extending axially from a thick portion of said ring and a free end which is bent in a direction radially inwardly of the axis of the adapter so as to provide a portion thereof protruding radially inwardly of the adapter adapted to engage and be deflected by the ring electrode on the small size terminal electrode assembly.

17. The adapter of claim 16 wherein said tubular body has annular sealing means extending thereabout adapted to engage the cylindrical surface within the terminal electrode assembly socket in the pacer and create a seal between the inner cylindrical surface of said socket and the outer surface of the adapter.

18. The adapter of claim 17 wherein said annular sealing means comprises an annular ring having a diameter greater than the inner diameter of the terminal electrode assembly socket in the pacer and being made of a resilient material so that it can flex inwardly when the adapter is inserted into the terminal electrode assembly socket in the pacer, and an annular groove in said tubular body adjacent said annular sealing ring to facilitate bending of the annular sealing ring toward the groove when said adapter is inserted into the electrode assembly socket in the pacer.

19. The adapter of claim 17 combined with a small size terminal electrode assembly which has annular sealing rings on the outer periphery thereof between the pacing lead and the ring electrode engaging and forming a seal with the inner cylindrical surface of the socket within the adapter defined by the inner diameter of the tubular body.

20. The adapter of claim 15 wherein one end of said ring has a thicker portion which abuts the proximal end of said tubular body and said at least one contact element extends from said thicker ring portion into said tubular body.

21. The adapter of claim 1 including a barrel member made of insulating material and having a first cylindrical cavity of one diameter extending substantially through the barrel member and a second cylindrical cavity of reduced diameter, said second electrical coupling means comprising a tube of electrically conductive material having one end thereof fixed within said second cylindrical cavity of said barrel member and with the remainder of said tube extending outwardly therefrom, said tube being adapted to receive and make electrical contact with a pin electrode at one end of the small size terminal electrode assembly and having an outer surface adapted to be received in and make contact with a conductive socket at one end of the terminal electrode assembly socket in the pacer.

22. The adapter of claim 1 wherein said adapter is constructed of materials generally inert to bodily fluids.

* * * * *